United States Patent [19]

Böger et al.

[11] Patent Number: 4,618,608

[45] Date of Patent: Oct. 21, 1986

[54] OXADIAZINES AND PESTICIDAL COMPOSITIONS CONTAINING THEM

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[21] Appl. No.: 789,677

[22] Filed: Oct. 21, 1985

[30] Foreign Application Priority Data

Oct. 31, 1984 [CH] Switzerland .................. 5208/84

[51] Int. Cl.$^4$ .................. C07D 273/04; A01N 43/72
[52] U.S. Cl. .................. 514/235; 514/234; 514/238; 544/67
[58] Field of Search .................. 547/67; 514/234, 235, 514/238

[56] References Cited

U.S. PATENT DOCUMENTS

| | | | |
|---|---|---|---|
| 4,150,158 | 4/1979 | Huff | 544/67 X |
| 4,348,394 | 9/1982 | Sirrenberg et al. | 544/67 X |
| 4,456,682 | 8/1985 | Sirrenberg et al. | 544/67 X |
| 4,459,297 | 7/1984 | Lange et al. | 424/248.58 |
| 4,468,405 | 8/1984 | Rigterink et al. | 424/322 |
| 4,536,341 | 8/1985 | Rigterink et al. | 260/253 |
| 4,550,108 | 10/1985 | Böger et al. | 544/67 X |

*Primary Examiner*—Richard L. Raymond
*Attorney, Agent, or Firm*—Edward McC. Roberts; Kevin T. Mansfield

[57] ABSTRACT

The invention relates to novel N-phenyl-1,3,5-oxadiazine-2,4-diones of formula I

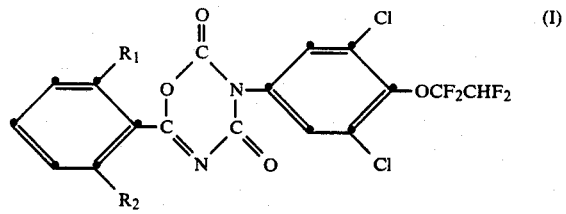

wherein
$R_1$ is fluorine or chlorine and
$R_2$ is hydrogen, fluorine or chlorine, to the preparation thereof, to the use thereof in pest control and to pesticidal compositions which contain said oxadiazines. The preferred field of application is the control of pests of animals and plants.

10 Claims, No Drawings

OXADIAZINES AND PESTICIDAL COMPOSITIONS CONTAINING THEM

The present invention relates to novel N-phenyl-1,3,5-oxadiazine-2,4-diones, to the preparation thereof, to the use thereof in pest control and to pesticidal compositions which contain said oxadiazines.

Those N-phenyl-1,3,5-oxadiazine-2,4-diones wherein the N-phenyl ring is not substituted simultaneously in the 3,5-position by Cl and in the 4-position by 1,1,2,2-tetrafluoroethoxy are known from German Offenlegungsschrift No. 2 905 687 as insecticides.

The oxadiazines of the present invention are of formula I

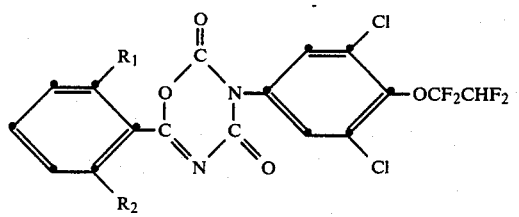

wherein
$R_1$ is fluorine or chlorine and
$R_2$ is hydrogen, fluorine or chlorine.

Preferred compounds of formula I are those wherein $R_1$ and $R_2$ are identical and are fluorine or chlorine.

An example of a compound of formula I is:

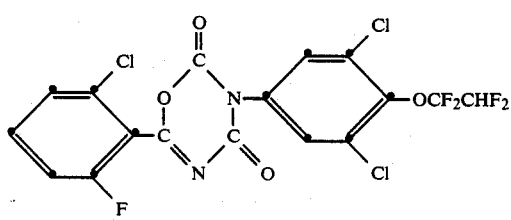

The compounds of the present invention can be prepared by methods known per se. Such methods are described, inter alia, in German Offenlegungsschrift specifications Nos. 2 732 115 and 2 905 687. Thus, for example, the compounds of formula I can be obtained by reacting a benzoylisocyanate of formula II

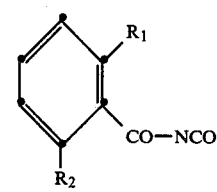

with the isocyanate of formula III

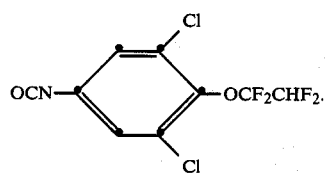

In order to carry out the process, the two reaction components are heated for 30 minutes to 30 hours to a temperature in the range from 50° to 150° C., preferably for 5 to 15 hours to a temperature in the range from 80° to 120° C., in the absence or presence of a solvent or diluent. Suitable solvents or diluents are in particular polar aprotic solvents such as dimethyl sulfoxide, dimethylformamide or N,N-dimethylacetamide.

The compounds of the present invention can also be prepared by other methods, e.g. by (a) condensing a halocarbonylbenzamide of formula IV

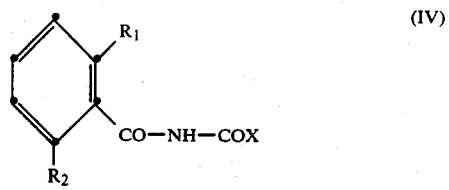

with the isocyanate of formula III, or (b) condensing a benzoylisocyanate of formula II with a carbamate of formula V

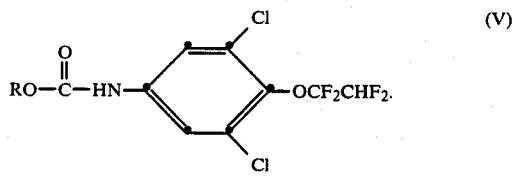

In formulae II, IV and V, the radicals $R_1$ and $R_2$ are as defined for formula I, and X is halogen, preferably chlorine, and R is an alkyl radical, preferably a lower alkyl radical containing 1 to 4 carbon atoms.

The compounds of formulae II to V are known or they can be prepared by known methods. Thus the benzylisocyanates of formula II can be obtained by reacting the suitably substituted benzamides with oxalyl chloride and the isocyanate of formula III can be obtained by reacting the suitably substituted aniline with phosgene.

Compared with the compounds known from German Offenlegungsschrift No. 2 905 687, the compounds of the present invention surprisingly exhibit a superior action against *Heliothis virescens* and *Spodoptera littoralis*. Quite generally they are valuable substances for controlling pests, while being well tolerated by warm-blooded animals and plants. The compounds of formula I are therefore suitable e.g. for controlling pests on animals and plants. Such pests belong principally to the phylum of Arthropoda, such as in particular insects of the orders Lepidoptera, Coleoptera, Homptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, e.g. in fruit and vegetable crops, and especially in cotton crops. If compounds of formula I are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the compounds of the invention are suitable above all against ectoparasites, e.g. mites and ticks and Diptera such as *Lucilia sericata*. The good activity of the compounds of the invention corresponds to a mortality of at least 50–60% of the above pests.

The activity of the compounds of the invention and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I can also be combined with particular advantage with substances which exert a pesticidally potentiating effect. Examples of such compounds are, inter alia, piperonyl butoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of formula I are used in unmodified form, or preferably together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethyene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1981; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1

Preparation 1.1.

3,5-Dichloro-4-(1,1,2,2-tetrafluoroethoxy)-phenylisocyanate 33.4 g of 3,5-dichloro-4-(1,1,2,2,-tetrafluoroethoxy)aniline are dissolved in 130 ml of chlorobenzene. With stirring, this solution is added dropwise at 22° C. to a solution consisting of 90 g of toluene containing 20% by weight of phosgene and of 100 ml of dioxane and 300 ml of chlorobenzene. The reaction mixture is stirred for 1 hour at room temperature, 1 hour at 50° C. and then 1 hour at 80° C. The reaction mixture is subsequently concentrated in a water-jet vacuum and then distilled under high vacuum, affording the title compound of the formula

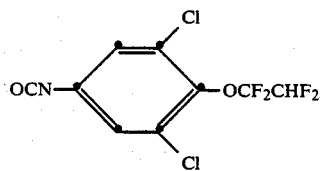

(III)

as a colourless oil. Boiling point 81°–83° C./2.5 mbar.

1.2.

3-[3,5-Dichloro-4-(1,1,2,2-tetrafluoroethoxy)phenyl]-6-(2,6-difluorophenyl)-3,4-dihydro-2H-1,3,5-oxadiazine-2,4-dione With the exclusion of moisture, 5.4 g of 2,6-difluorobenzoylisocyanate are added with stirring to 9.1 g of 3,5-dichloro-4-(1,1,2,2-tetrafluoroethoxy)-phenylisocyanate. The temperature is maintained at 120° C. for 14 hours, with stirring being continued until the reaction mixture commences to congeal. When the resultant crystalline slurry has cooled to room temperature, it is triturated with hexane and subsequently filtered with suction. The residue is recrystallised from toluene, affording the title compound of the formula

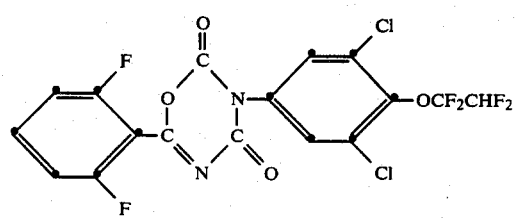

as a white powder with a melting point of 170°–172° C. (compound 1.2.1).

The following compounds are prepared in analogous manner:

| Compound | $R_1$ | $R_2$ | m.p. °C. |
|---|---|---|---|
| 1.2.2 | Cl | Cl | 182–184 |
| 1.2.3 | Cl | H | 167–169 |
| 1.2.4 | F | H | 166–168 |

EXAMPLE 2

Formulation Examples for active ingredients of formula I according to Preparatory Example 1 (throughout, percentages are by weight)

| 2.1. Emulsifiable concentrates | (a) | (b) | (c) | (d) |
|---|---|---|---|---|
| a compound according to Preparatory Example 1 | 10% | 25% | 40% | 50% |
| calcium dodecylbenzenesulfonate | — | 5% | 8% | 6% |
| castor oil polyethylene glycol ether (36 moles of ethylene oxide) | — | 5% | — | — |
| tributylphenol polyethylene glycol ether (30 moles of ethylene oxide) | — | — | 12% | 4% |
| castor oil thioxilate | 25% | — | — | — |
| cyclohexanone | — | — | 15% | 20% |
| butanol | 15% | — | — | — |
| xylene mixture | — | 65% | 25% | 20% |
| ethyl acetate | 50% | — | — | — |

Emulsions of any required concentration can be produced from such concentrates by dilution with water.

| 2.2. Solutions | (a) | (b) |
|---|---|---|
| a compound according to Preparatory Example 1 | 10% | 5% |
| ethylene glycol monomethyl ether | — | — |
| polyethylene glycol 400 | 70% | — |
| N—methyl-2-pyrrolidone | 20% | — |
| epoxidised coconut oil | — | 1% |
| petroleum distillate (boiling range 160–190° C.) | — | 94% |

These solutions are suitable for application in the form of microdrops.

| 2.3. Granulates | (a) | (b) |
|---|---|---|
| a compound according to Preparatory Example 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) | (c) | (d) |
|---|---|---|---|---|
| a compound according to Preparatory Example 1 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient.

| 2.5. Wettable powders | (a) | (b) | (c) |
|---|---|---|---|
| a compound according to Preparatory Example 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Extruder granulate | |
|---|---|
| a compound according to Preparatory Example 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.7. Coated granulate | |
|---|---|
| a compound according to Preparatory Example 1 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.8. Suspension concentrate | |
|---|---|
| a compound according to Preparatory Example 1 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological Test

3.1. Action against *Musca domestica*

50 g of freshly prepared CSMA nutrient substrate for maggots are charged into a beaker. 5 ml of a 1% acetonic solution of the test compound is pipetted onto the nutrient substrate present in the beaker. The substrate is then thoroughly mixed and the acetone subsequently allowed to evaporate over a period of at least 20 hours.

Then 25 one-day-old maggots of *Musca domestica* are put into the beaker containing the treated nutrient substrate. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds according to Example 1 exhibit good activity in this test.

3.2. Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, the compounds according to Example 1 exhibit good activity against *Lucilia sericata*.

3.3. Action against *Aedes aegypti*

A concentration of 12.5 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 2 and 7 days.

The compounds according to Example 1 exhibit good activity in this test.

3.4. Insecticidal action against feeding insects

Cotton plants (about 20 cm high) are sprayed with an aqueous emulsion (obtained from a 10% emulsifiable concentrate) containing 100 ppm of the test compound. After the spray coating has dried, the cotton plants are populated with *Spodoptera littoralis* and *Heliothis virescens* larvae in the $L_3$-stage. The test is carried out at 24° C. and 60% relative humidity. At 24 hour intervals, a mortality count is made and the larvae are also examined for inhibition of development and moulting.

The compounds according to Example 1 exhibit good activity in this test.

3.5. Action against *Spodoptera littoralis* and *Heliothis virescens* (larvae and eggs)

Three cotton plants each having a height of about 15-20 cm and grown in pots are treated with a sprayable liquid preparation of the test compound. After the spray coating has dried, the potted plants are placed in a metal container having a capacity of about 20 liters and covered with a glass plate. The humidity in the interior of covered container is regulated such that no water of condensation forms. Direct light falling on the plants is avoided. The three plants are then infested altogether with:

(a) 50 larvae of *Spodoptera littoralis* or *Heliothis virescens* in the $L_1$-stage;
(b) 20 larvae of *Spodoptera littoralis* or *Heliothis virescens* in the $L_3$-stage;
(c) 2 eggs deposits of *Spodoptera littoralis* or *Heliothis virescens*. (The procedure is that two leaves of each plant are put into a plexiglass cylinder sealed at both ends with gauze. Two egg deposits of Spodoptera, or a part of a cotton leaf with eggs of Heliothis deposited thereon, are added to the leaves sealed in the cylinder.)

Evaluation in comparison with untreated controls is made after 4 to 5 days, taking into account the following criteria:
(a) the number of still living larvae,
(b) inhibition of larval development and moulting,
(c) feeding damage (shredding and perforation damage),
(d) hatching rate (number of larvae hatched from the eggs).

In this test, the compounds according to Example 1 exhibit good overall activity at a concentration of 400 ppm.

3.6. Ovicidal action against *Spodoptera littoralis*

Eggs of *Spodoptera littoralis* deposited on filter paper are cut out of the paper and immersed in a 0.05% by weight solution of the test compound in a 1:1 mixture of acetone-water. The treated deposits are then removed from this mixture and kept in plastic dishes at 28° C. and 60% humidity. The hatching rate, i.e. the number of larvae which have developed from the treated eggs, is determined after 5 days.

The compounds according to Example 1 show good activity in this test.

3.7. Action against *Laspeyresia pomonella* (eggs)

Egg deposits of *Laspeyresia pomonella* not more than 24 hours old are immersed on filter paper for 1 minute in an aqueous acetonic solution containing 400 ppm of the test compound.

After the solution has dried, the filter paper and the eggs are placed in petri dishes and kept at a temperature of 28° C. The percentage of larvae hatched from the treated eggs is evaluated after 6 days.

The compounds according to Example 1 exhibit good activity in this test.

3.8. Influence on the reproduction of *Anthronomus grandis*

*Anthonomus grandis* adults which are not more than 24 hours old after hatching are transferred in groups of 25 to barred cages. The cages are then immersed for 5 to 10 seconds in acetonic solution containing 0.1% by weight of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

The compounds according to Example 1 exhibit a good reproduction inhibiting effect in this test.

3.9. Action against *Anthonomus grandis* (adults)

Two cotton plants in the 6-leaf stage, in pots, are each sprayed with a wettable aqueous emulsion formulation containing 100 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

The compounds according to Example 1 exhibit good activity in this test.

What is claimed is:

1. A compound of formula I

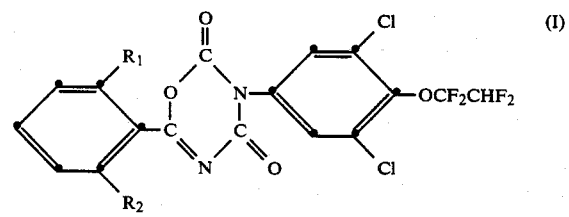

wherein
$R_1$ is fluorine or chlorine and
$R_2$ is hydrogen, fluorine or chlorine.

2. A compound of formula I according to claim 1, wherein $R_1$ and $R_2$ are identical and are fluorine or chlorine.

3. The compound according to claim 2 of the formula

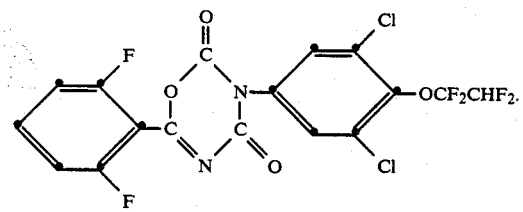

4. The compound according to claim 2 of the formula

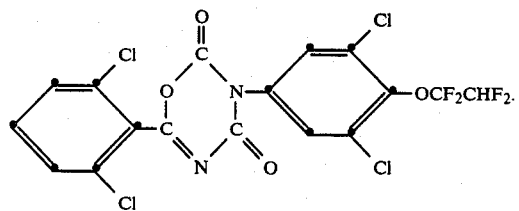

5. The compound according to claim 1 of the formula

6. The compound according to claim 1 of the formula

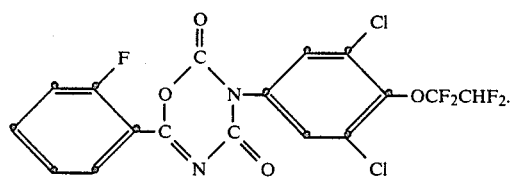

7. A pesticidal composition which contains as active ingredient a compound of formula I

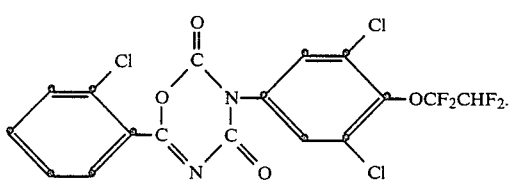

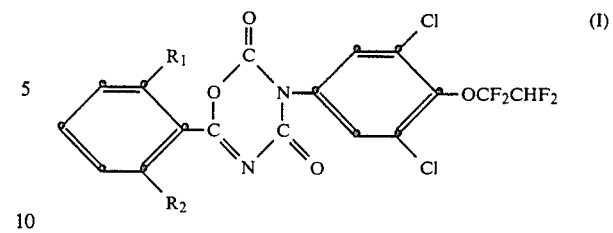

wherein
R₁ is fluorine or chlorine and
R₂ is hydrogen, fluorine or chlorine,
together with suitable carriers and/or adjuvants.

8. A method of controlling pests of animals and plants, which method comprises applying to said animals and plants or to the locus thereof a pesticidally effective amount of a compound of formula I

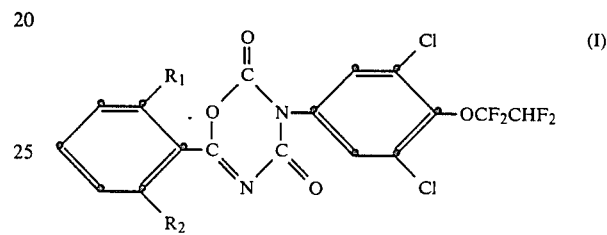

wherein
R₁ is fluorine or chlorine and
R₂ is hydrogen, fluorine or chlorine.

9. A method according to claim 8 of controlling arthropods.

10. A method according to claim 8 of controlling plant-destructive insects and arachnids.

* * * * *